United States Patent [19]

Oppenlaender et al.

[11] Patent Number: 5,250,225
[45] Date of Patent: Oct. 5, 1993

[54] AMMONIUM SALT OF AN ALKENYLSUCCINIC HALF-AMIDE AND THE USE THEREOF AS CORROSION INHIBITOR IN OIL AND/OR GAS PRODUCTION TECHNOLOGY

[75] Inventors: Knut Oppenlaender, Ludwigshafen; Brigitte Wegner, Speyer; Wilhelmus Slotman, Ludwigshafen, all of Fed. Rep. of Germany

[73] Assignee: BASF Aktiengesellschaft, Ludwigshafen, Fed. Rep. of Germany

[21] Appl. No.: 7,819

[22] Filed: Jan. 22, 1993

Related U.S. Application Data

[63] Continuation of Ser. No. 822,265, Jan. 17, 1992, abandoned.

[30] Foreign Application Priority Data

Feb. 4, 1991 [DE] Fed. Rep. of Germany ....... 4103262

[51] Int. Cl.$^5$ ............................................. C23F 11/06
[52] U.S. Cl. ................. 252/389.62; 252/392; 252/8.555; 422/16; 544/35; 544/36; 562/571
[58] Field of Search ............... 252/389.62, 392, 8.555; 544/35, 36; 562/571; 422/16

[56] References Cited

U.S. PATENT DOCUMENTS

| | | |
|---|---|---|
| 4,436,639 | 3/1984 | Oppenlaender et al. ......... 252/8.555 |
| 4,517,114 | 5/1985 | Oppenlaender et al. ..... 252/8.555 X |
| 4,609,531 | 9/1986 | Ritschel et al. .................. 252/392 X |
| 4,722,812 | 2/1988 | Ritschel et al. .................. 252/392 X |
| 4,724,124 | 2/1988 | Ritschel et al. .................. 252/392 X |
| 4,729,841 | 3/1988 | Ritschel et al. .................. 252/392 X |
| 5,037,565 | 8/1991 | King ....................................... 252/25 |

FOREIGN PATENT DOCUMENTS

| | | |
|---|---|---|
| 065191 | 5/1982 | European Pat. Off. . |
| 103737 | 8/1983 | European Pat. Off. . |
| 0106234 | 9/1983 | European Pat. Off. . |
| 359048 | 8/1989 | European Pat. Off. . |
| 2943963 | 10/1979 | Fed. Rep. of Germany . |
| 3300874 | 7/1984 | Fed. Rep. of Germany . |

OTHER PUBLICATIONS

Effect of Elemental Sulfur on the Performance of Nitrogen-Based Oilfield Corrosion Inhibitors, Kennelley et al., Environment Treatment & Control Feb. 1990, 48-52.

*Primary Examiner*—Robert L. Stoll
*Assistant Examiner*—Valerie D. Fee
*Attorney, Agent, or Firm*—Keil & Weinkauf

[57] ABSTRACT

An ammonium salt of an alkenylsuccinic half-amide of formula (I) below

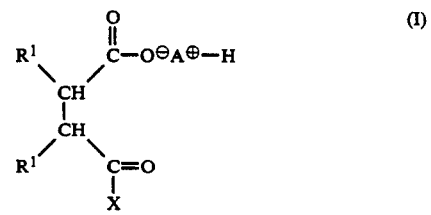

in which $R^1$ denotes H or a $C_6$–$C_{18}$-alkenyl radical, provided that the radicals $R^1$ are not both H or both $C_6$–$C_{18}$-alkenyl, X denotes a group of the formula —$NHR^2$ or —$NR^2R^3$, in which $R^2$ and $R^3$ denote $C_1$–$C_6$-alkyl, cycloalkyl or a heterocyclic ring attached to the nitrogen atom via an alkylene chain, and A denotes XH or a different primary, secondary, or tertiary amine, for example an alkanolamine or a polyamine, and the use thereof as a corrosion inhibitor in oil and/or gas production technology.

9 Claims, No Drawings

AMMONIUM SALT OF AN ALKENYLSUCCINIC HALF-AMIDE AND THE USE THEREOF AS CORROSION INHIBITOR IN OIL AND/OR GAS PRODUCTION TECHNOLOGY

This application is a continuation of application Ser. No. 07/822,265, filed on Jan. 17, 1992 now abandoned.

The invention relates to ammonium salts of alkenyl succinic half-amides and to the use thereof as corrosion inhibitors in oil and/or gas production technology to combat corrosion by media containing $CO_2$ and $H_2S$ and possibly elemental sulfur.

In the production of petroleum and natural gas there usually occurs an oil/water or gas/water mixture which in the case of oil may contain up to about 98% of water.

The salinity of the entrained water may be extremely low or conversely, the water may comprise a saturated salt solution. $H_2S$ and/or $CO_2$ are also present.

The combination of $H_2S$ and/or $CO_2$ and the water has a strong corrosive action on metals used in petroleum and natural gas plants. This action is intensified by the presence of elemental sulfur.

It is common practice to inject a solution or dispersion of corrosion inhibitor into the corrosive medium to be handled in the production, transport and storage of petroleum or natural gas. By this means the surface of the metals contacted by the medium is coated with a protective film.

Hitherto, certain imidazoline salts have been proposed for this purpose (cf. EP 0,065,191 and EP 0,103,737), but these have an unsatisfactory anticorrosive effect against $CO_2$ and/or $H_2S$, especially in the presence of elemental sulfur, as discussed in *Environment Treatment & Control*, Feb. 1990, pp. 48 to 52.

Neither do amine salts of maleamide acids, as described in EP 0,106,234, possess adequate anticorrosive properties for this purpose.

Oil-soluble amidoamine salts of alkenylsuccinic acids and the use thereof as corrosion inhibitors in water-in-oil emulsions such as occur in oil production are described in EP 0,359,048.

Water-soluble alkanolamine salts of alkenylsuccinic acids, described in DE 2,943,963-C2 as being effective as corrosion inhibitors in metal working, also show inadequate, anticorrosive action in the systems under consideration here.

It is thus an object of the invention to provide improved, preferably water-soluble inhibitors for use in corrosive media such as occur in petroleum and/or natural gas production, to counteract the corrosive action of $CO_2$ and/or $H_2S$, especially when elemental sulfur is present.

We have now found that ammonium salts of alkenylsuccinic half-amides of formula (I) below

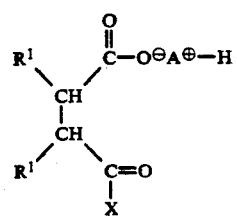

in which $R^1$ denotes H or a $C_6$–$C_{18}$-alkenyl radical, provided that the radicals $R^1$ are not both H or both $C_6$–$C_{18}$-alkenyl, X denotes a group of the formula $-NHR^2$ or $-NR^2R^3$, in which $R^2$ and $R^3$ denote $C_1$–$C_6$-alkyl, cycloalkyl or a heterocyclic ring attached to the nitrogen atom via an alkylene chain, and A denotes XH or a different amine of the formula

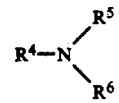

in which $R^4$, $R^5$ and $R^6$ independently denote H, $C_1$–$C_6$-alkyl (in which case $R^5$ and $R^6$ may together form a heterocyclic ring enclosing the nitrogen atom), $C_1$–$C_{10}$-hydroxyalkyl or

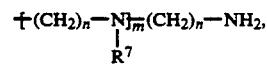

in which $R^7$ denotes H or $C_1$–$C_3$-alkyl, n is an integer from 2 to 4, and m is an integer from 1 to 5, are particularly well suited for use as water-soluble corrosion inhibitors in oil and/or gas production plants.

A particularly suitable representative of the group X is a group of the formula (II) below

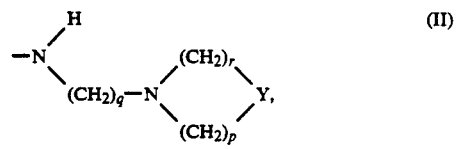

in which q is an integer from 1 to 4, r and p are independently 1 or 2, and Y denotes $CR^8_2$, $NR^8$ (where $R^8$ is H or $C_1$–$C_3$-alkyl), O or S.

It is particularly advantageous when the group X is a radical of formula (III) below:

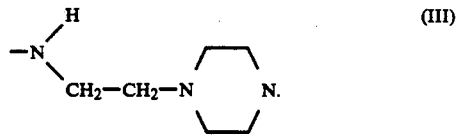

The counterion A⊕—H is derived either from the amine XH used to form the half-amide or from a different amine of the formula

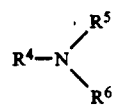

in which $R^4$, $R^5$ and $R^6$ have the meanings stated above. Such amines are $NH_3$ or primary, secondary, or tertiary amines, e.g. butylamine or dibutylamine, or alkanolamines, e.g. ethanolamine, diethanolamine, or triethanolamine, or they are polyamines such as diethylenetriamine or dipropylenetriamine.

The alkenylsuccinic amides forming the basis of the salts of the invention are obtained by the following method:

1. The endothermic reaction, known per se, between maleic anhydride and the appropriate olefin is carried out at a temperature of from 150° to 250° C. under standard pressure conditions or at a temperature of from 150° to 300° C. in an autoclave (as described in, say, DE-A 3,411,531) and
2. the alkenylsuccinic anhydride thus obtained is reacted with the amine XH to form the alkenylsuccinic half-amide at a temperature of from 50° to 150° C., preferably from 50° to 120° C., for example in substance or in an aromatic solvent.

The amide/ammonium salts of the invention are obtained therefrom by reaction with the amines A, preferably also at a temperature of from 50° to 120° C. When the same amine components are used for XH and A, the preparation of the amide/ammonium salt may be effected directly by reacting the alkenylsuccinic anhydride with the amine in a ratio of 1:2.

Particularly noteworthy examples of amines XH are aminoalkylpiperazines and aminoalkylmorpholines, for example aminoethylpiperazine.

The inhibitors thus obtained exhibit excellent anticorrosive action against $H_2S$ and $CO_2$, and in particular, no impairment of this action is caused by the presence of elemental sulfur.

The efficacy of the inhibitors, particularly in the presence of elemental sulfur, can be increased by formulating the products with surface-active substances.

Suitable dispersing agents are: low molecular-weight or polymeric anionic surfactants and dispersing agents, particularly alkylsulfonic acids, alkylarylsulfonic acids, arylsulfonic acids, and the salts thereof.

The corrosion inhibitors of the invention are used in amounts varying from 3 to 1000 ppm depending on the composition of the corrosive medium. To combat corrosion by $CO_2$ or $CO_2/H_2S$ only, the addition of inhibitor formulation is preferably from 5 to 50 ppm, and in the presence of elemental sulfur it is preferably from 100 to 300 ppm.

The invention is illustrated by the following Examples.

1. AMMONIUM SALT SYNTHESIS

Example 1

2.3 g of phenothiazine were added to a reaction mixture of equimolar amounts of tetrameric propylene (463 g) and maleic anhydride (269.5 g), and the whole was stirred at a temperature of from 180° to 200° C. over a period of from 25 to 30 hours. Unconverted educts were then distilled off at 175° C. under a high vacuum.

A mixture of 342 g of the resulting alkenylsuccinic anhydride and 400 ml of xylene was heated to 80° C., and 368 g of aminoethylpiperazine were added dropwise at this temperature. Stirring was continued for 3 hours at the same temperature, and a portion of the solvent was removed under a water jet vacuum. There was obtained a black viscous product in a yield of 608 g and having a content of 85% of active ingredient.

The tetrameric propylene used was the $C_{12}$ cut from the olefin oligomerization.

Composition (GC/MS analysis): $C_9$ 0.5%; $C_{10}$ 5.8% $C_{11}$ 20.7%; $C_{12}$ 70.9%; $C_{13}$ 2.1%.

The composition and isomer ratio may vary slightly from batch to batch.

The IR spectrum clearly indicates that the reaction product obtained from the alkenylsuccinic anhydride and aminoethylpiperazine is an ammonium salt of the alkenylsuccinic half-amide, since it shows both characteristic amide bands and $—CO_2$ bands. Imide formation is also indicated.

Characteristic IR bands:
Amide: 1680 to 1630 and 1570 to 1515 cm$^{-1}$
COO—: 1610 to 1550 cm$^{-1}$
Imide: approx. 1770 to approx. 1700 cm$^{-1}$.

The ammonium salts of the invention can be isolated from the reaction solution by conventional means.

Example 2

387 g of trimeric butylene (prepared by trimerization of n-butene) and 225 g of maleic anhydride were placed in an autoclave. A nitrogen pressure of 5 bar was established, and the reaction mixture was stirred for 10 hours at a temperature of 200° C.

595 g of the reaction product were dissolved in 300 ml of xylene, and the solution was heated to 80° C. 578 g of aminoethylpiperazine were added dropwise at this temperature. The reaction mixture was stirred for 4 hours at the same temperature, after which a portion of the solvent was removed under a water jet vacuum to give the desired corrosion inhibitor as a dark-colored viscous oil.

Example 3

Example 2 was repeated except that a linear $C_{12}$-olefin was used in place of trimeric butylene.

Example 4

An alkenylsuccinic anhydride was prepared from trimeric butylene and maleic anhydride as described in Example 2. Unconverted olefin and anhydride were removed at 100° C./30 mbar.

198 g (0.75 mole) of this product were dissolved in xylene, and the solution was heated to 100° C. 97 g (0.75 mole) of aminoethylpiperazine were slowly added dropwise at this temperature. The reaction solution was then stirred for about 5 hours at 90°–100° C. The solvent was then removed to give 290 g of a black viscous reaction product.

In order to neutralize the free carboxyl groups, 101 g (0.2 mole) of this product were reacted with 26 g (0.2 mole) of diethylenetriamine in xylene at 80° C. The product was concentrated in a rotary evaporator to about 83% to give the corrosion inhibitor of the invention in the form of a black viscous oil.

2. EXAMPLES OF APPLICATION

The inhibitor formulations were tested dynamically using the "wheel-test" described, for example, in EP-A 0,359,048, which is a common method of testing corrosion inhibitors in petroleum and natural gas production plants. The test coupons were large steel plates of ST 37 which had previously been thoroughly ground with emery, degreased with toluene, and weighed.

The coupons were then placed in the corrosive medium and were agitated therein for 16 hours at 80° C. (40 rpm via a shaft coupled to rotate the test vessel). The specimens were then cleaned with an inhibited acid, degreased, dried, and weighed in order to determine the weight loss. The results were compared with reference values obtained in a test carried out without the addition of inhibitor.

The anticorrosive factor Z in percent was calculated from the weighings using the following equation:

$$Z = \frac{G_0 - G_1}{G_0} \times 100[\%]$$

where $G_0$ is the rate of corrosion without inhibitor and $G_1$ is the rate of corrosion with inhibitor.

The results are listed in the Tables below.

TABLE 1

Anticorrosive factor Z [%]

Medium:
10% white spirit, 90% brine (3% NaCl); saturated with $CO_2$ and/or $H_2S$

| Saturated with: | $CO_2/CO_2$ | | $CO_2/H_2S$ | |
|---|---|---|---|---|
| Inhibitor dosage: | 3ppm | 7.5 ppm | 3 ppm | 7.5 ppm |
| Product from | | | | |
| Example 1 | 46 | 78 | 68 | 79 |
| Example 2 | 51 | 75 | 74 | 80 |
| Example 3 | 61 | 64 | 76 | 81 |
| Example 4 | | | 80 | 80 |

TABLE 2

Medium: approx. 6.5 ml of brine saturated with $H_2S$, approx. 193.5 ml of brine saturated with $CO_2$, 0.5 g of ground sulfur Inhibitor dosage: 150 ppm

| Product from | Dispersing agent | Anticorrosive factor Z [%] |
|---|---|---|
| Example 1 | — | 50 |
| Example 1 | 10% oligomeric aryl sulfonate (Tamol 9410 ®) | 82 |
| Example 1 | 15% alkylbenzene sulfonate (ALBS) | 78 |
| Example 2 | 10% oligomeric aryl sulfonate | 85 |
| Example 2 | 15% ALBS | 78 |
| Example 3 | 15% ALBS | 80 |
| Example 3 | 10% oligomeric aryl sulfonate | 75 |
| Example 4 | 15% ALBS | 80 |

COMPARATIVE EXAMPLES

Medium: approx. 6.5 ml of brine saturated with $H_2S$, approx. 193.5 ml of brine saturated with $CO_2$, 0.5 g of ground sulfur Inhibitor dosage: 150 ppm

| Product | Dispersing agent | Anticorrosive factor [%] |
|---|---|---|
| 1. acetate of a long-chain imidazoline | — | 17 |
| 2. amido-imidazoline plus dimerized/trimerized fatty acid | — | 33 |
| 3. amido-imidazoline | — | 25 |
| 4. as for 1 | 10% oligomeric aryl sulfonate | 0 |
| 5. as for 1 | 15% alkylbenzene sulfonate | 12 |

It can be seen from the above results that the commercially available corrosion inhibitors are distinctly less effective and that the addition of dispersing agents to said prior art corrosion inhibitors has no advantageous effect.

By comparison, the ammonium salts of the invention are found to be highly effective corrosion inhibitors.

We claim:

1. An ammonium salt of an alkenylsuccinic half-amide of formula (I) below

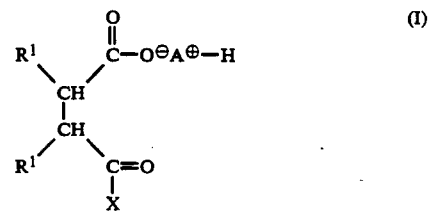

in which
R¹ denotes H or a $C_6$-$C_{18}$-alkenyl radical, provided that the radicals
R¹ are not both H or both $C_6$-$C_{18}$-alkenyl,
X denotes a group of the formula (II)

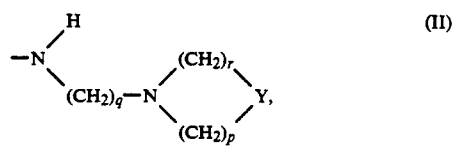

in which q is an integer from 1 to 4, r and p are independently 1 or 2, and Y denotes $CR^8_2$, $NR^8$ (where $R^8$ is H or $C_1$-$C_3$-alkyl), O or S, and
A denotes XH or a different amine of the formula

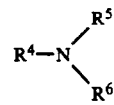

in which
$R^4$, $R^5$ and $R^6$ independently denote H, $C_1$-$C_6$-alkyl or
$R^5$ and $R^6$ together form a heterocyclic ring enclosing the nitrogen atom, $C_1$-$C_{10}$-hydroxyalkyl or

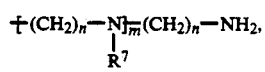

in which $R^7$ denotes H or $C_1$-$C_3$-alkyl,
n is an integer from 2 to 4, and
m is an integer from 1 to 5.

2. An ammonium salt of the formula (II) as set forth in claim 1, in which
X denotes a group of formula (III)

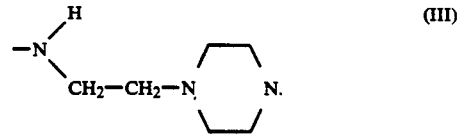

3. An anti-corrosive formulation which contains an ammonium salt as defined in claim 1 and a dispersing agent.

4. The anticorrosive formulation as defined in claim 3, wherein the dispersing agent is a low molecular-weight or polymeric anionic surfactant, selected from the group consisting of an alkylsulfonic acid, an alkylarylsulfonic acid, and/or an arylsulfonic acid, and/or a salt of said acids.

5. An anti corrosive formulation as defined in claim 3 where X denotes a group of the formula below

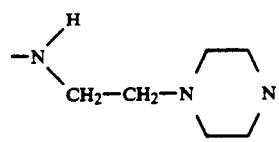

6. A method of inhibiting corrosion in metals which are in contact with corrosive oil/water or gas/water mixtures found in the production, transport and storage of petroleum and natural gas which comprises: injecting into the corrosive mixture a corrosion inhibiting amount of an ammonium salt of an alkenyl succinic half amide of the formula (I) as defined below,

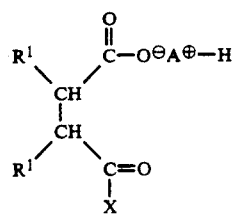
(I)

in which
$R^1$ denotes H or a $C_6$-$C_{18}$-alkenyl radical, provided that the radicals $R^1$ are not both H or both $C_6$-$C_{10}$-alkenyl,
X denotes a group of the formula (II)

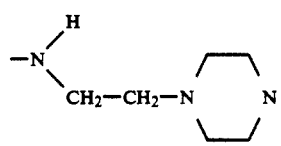
(II)

in which q is an integer from 1 to 4, r and p are independently 1 or 2, and Y denotes $CR^8_2$, $NR^8$ (where $R^8$ is H or $C_1$-$C_3$-alkyl), O or S, and
A denotes XH or a different amine of the formula

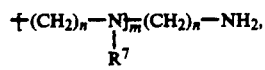

in which
$R^4$, $R^5$ and $R^6$ independently denote H or $C_1$-$C_6$-alkyl or $R^5$ and $R^6$ together form a heterocyclic ring including the nitrogen atom, $C_1$-$C_{10}$-hydroxyalkyl or $$+(CH_2)_n-N\overline{)_m}(CH_2)_n-NH_2,$$
$$\phantom{+(CH_2)_n-N}|\phantom{(CH_2)_n-NH_2,}$$
$$\phantom{+(CH_2)_n-N}R^7$$

in which $R^7$ denotes H or $C_1$-$C_3$-alkyl,
n is an integer from 2 to 4, and
m is an integer from 1 to 5.

7. A method of inhibiting corrosion in metals which are in contact with corrosive oil/water or gas/water mixtures found in the production, transport and storage of petroleum and natural gas which comprises: injecting into the corrosive mixture a corrosion inhibiting amount of an ammonium salt of the formal (I) as defined in claim 6 where x denotes a group of the formula (II)

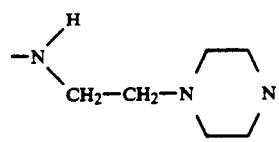
(II)

8. A method as defined in claim 6, wherein the corrosive medium contains $CO_2$ and/or $H_2S$.

9. A method as claimed in claim 8, wherein the corrosive medium also contains elemental sulfur.

* * * * *